United States Patent
Stefanov

(10) Patent No.: US 11,986,642 B2
(45) Date of Patent: May 21, 2024

(54) NEEDLE SHIELD REMOVER

(71) Applicant: SHL MEDICAL AG, Zug (CH)

(72) Inventor: Slobodan Stefanov, Deerfield Beach, FL (US)

(73) Assignee: SHL MEDICAL AG, Zug (CH)

( * ) Notice: Subject to any disclaimer, the term of this patent is extended or adjusted under 35 U.S.C. 154(b) by 696 days.

(21) Appl. No.: 16/972,507

(22) PCT Filed: Sep. 12, 2019

(86) PCT No.: PCT/EP2019/074298
§ 371 (c)(1),
(2) Date: Dec. 4, 2020

(87) PCT Pub. No.: WO2020/064337
PCT Pub. Date: Apr. 2, 2020

(65) Prior Publication Data
US 2021/0268200 A1    Sep. 2, 2021

Related U.S. Application Data

(60) Provisional application No. 62/735,313, filed on Sep. 24, 2018.

(30) Foreign Application Priority Data

Nov. 9, 2018 (EP) .................................. 18205314

(51) Int. Cl.
*A61M 5/32* (2006.01)
(52) U.S. Cl.
CPC .................................. *A61M 5/3204* (2013.01)

(58) Field of Classification Search
CPC .... A61M 5/32; A61M 5/3204; A61M 5/3202; A61M 5/3205; A61M 5/321; A61M 5/3213
See application file for complete search history.

(56) References Cited

U.S. PATENT DOCUMENTS 4,850,977 A * 7/1989 Bayless ............... A61M 5/3243
604/263
4,863,434 A * 9/1989 Bayless ............... A61M 5/3243
604/263

(Continued)

FOREIGN PATENT DOCUMENTS

CN    103974734 A    8/2014
CN    104114105 A    10/2014

(Continued)

OTHER PUBLICATIONS

International Search Report and Written Opinion for Int. App. No. PCT/EP2019/074298, dated Dec. 11, 2019.

*Primary Examiner* — Quynh-Nhu H. Vu
(74) *Attorney, Agent, or Firm* — McDonnell Boehnen Hulbert & Berghoff LLP

(57) ABSTRACT

A needle shield remover for assembly with a cap of a medicament delivery device is presented where the needle shield remover has a main body, at least a flexible first grabber, and at least a flexible second grabber. The first grabber and second grabber extend from the main body and are inclined in relation to the longitudinal axis of the needle shield remover such that they cross each other to form a receiving space configured to receive a delivery member shield.

13 Claims, 4 Drawing Sheets

(56) References Cited

U.S. PATENT DOCUMENTS

| | | | | |
|---|---|---|---|---|
| 5,098,400 | A | * | 3/1992 | Crouse ............... A61M 5/3204 604/263 |
| 5,304,151 | A | * | 4/1994 | Kuracina ............ A61M 5/3275 604/263 |
| 5,658,259 | A | * | 8/1997 | Pearson .............. A61M 5/2033 604/232 |
| 6,623,458 | B2 | * | 9/2003 | Woehr ................ A61M 5/3273 604/110 |
| 8,273,056 | B2 | * | 9/2012 | Kuracina ............ A61M 5/3273 604/110 |
| 9,233,212 | B2 | | 1/2016 | Holmqvist |
| 9,421,336 | B2 | * | 8/2016 | Ekman ................ A61M 5/3245 |
| 10,857,295 | B2 | * | 12/2020 | Huthmacher ....... A61M 5/2033 |
| 11,744,955 | B2 | * | 9/2023 | Huthmacher ....... A61M 5/3204 604/198 |
| 2007/0173772 | A1 | * | 7/2007 | Liversidge ............ A61M 5/326 604/192 |
| 2010/0004678 | A1 | | 1/2010 | Querol Garica |
| 2010/0018013 | A1 | | 1/2010 | Vermillion et al. |
| 2015/0134016 | A1 | | 5/2015 | Biedermann et al. |

FOREIGN PATENT DOCUMENTS

| | | |
|---|---|---|
| CN | 107485763 A | 12/2017 |
| CN | 107519559 A | 12/2017 |
| EP | 3257536 A1 | 12/2017 |
| GB | 2438593 A | 12/2007 |
| TW | 201726194 A | 8/2017 |
| WO | 2017/223354 A1 | 12/2017 |

\* cited by examiner

NEEDLE SHIELD REMOVER

CROSS REFERENCE TO RELATED APPLICATIONS

The present application is a U.S. National Phase application pursuant to 35 U.S.C. § 371 of International Application No. PCT/EP2019/074298 filed Sep. 12, 2019, which claims priority to U.S. Provisional Patent Application No. 62/735,313 filed Sep. 24, 2018, and European Patent Application No. 18205314.0 filed Nov. 9, 2018. The entire disclosure contents of these applications are herewith incorporated by reference into the present application.

TECHNICAL AREA

The present disclosure relates to a needle shield remover and in particular to a needle shield remover for a needle shield of a medicament delivery device that has at least two grabbers extending that cross each other to form a space configured to receive and catch the needle shield.

BACKGROUND

Today's medicament delivery devices may be complex and involves many different components. The physical features of each components and the way components are assembled together has a direct effect on how these components are going to interact with each other and on the success rate of the medicament delivery device in use.

One area is a removal of a cap on the medicament delivery device to pull the needle shield away from a medicament container, wherein the needle shield is initially attached to the medicament container (e.g. syringe) to cover and protect the injection member (e.g. the needle) on the medicament container. A successful needle shield removal involves two parts, namely the interaction between the cap and the needle shield remover as well as that between the needle shield remover and the needle shield. The cap needs to firmly grip the needle shield remover which in turn needs to firmly grip the needle shield in order for the user to successfully remove the needle shield by pulling the cap away from the medicament delivery device.

Currently, the needle shield remover includes prongs that extend radially inward and configured to claws into the needle shield when the user pulls the cap. In order for the needle shield remover to firmly grip the needle shield during removal, it is important for the prongs to be able to extend as much radially inward as possible in order to ensure that the prongs will claws deep into the needle shield. However, it is not guaranteed that the prongs will always firmly claws into the needle shield when the user pulls the cap and thus sometimes the prongs may fail to grip the needle shield which results in removal failure. The problem may be solved by making the prongs longer and thus increasing the chance of prongs clawing into the needle shield. However, making the prongs longer will also create the risk that the prongs become so long that the needle shield cannot be inserted into the needle shield remover by flexing the prongs radially outward. Thus, there is a need for a needle shield remover that can firmly grip the needle shield so that the user can pull both the needle shield remover and needle shield away from the medicament delivery device.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

In view of the foregoing, a general object of the present disclosure is to provide a needle shield remover for a cap of a medicament delivery device, which needle shield remover is easier to assemble.

These and other aspects of, and advantages with, the present disclosure will become apparent from the following detailed description of the present disclosure and from the accompanying drawings.

According to a main aspect of the disclosure it is characterized by a needle shield remover for assembly with a cap of a medicament delivery device. The needle shield remover comprises a main body, at least one flexible first grabber, and at least one flexible second grabber. The first and second grabbers both extend from the main body and are inclined in relation to a longitudinal axis such that they cross each other to form a receiving space configured to receive a delivery member shield.

The first grabber includes a first opening configured to allow the second grabber to pass through and cross the first grabber. On the other hand, the second grabber including a second opening, wherein the first opening and the second opening are configured for the delivery member shield to passes through and at least partially enter the main body. Further, the second grabber includes a limiting member configured to engage the first grabber and limit a radial movement of the first grabber relative to the second grabber.

Each of the first grabber and the second grabber including a grabber portion configured to engage the delivery member shield received in the receiving space. In one embodiment, each of the first grabber and the second grabber includes a pair of arms extending from the main body and connects to form the grabber portion. The delivery member shield is attached to a neck of a medicament container, the grabber portion has a neck portion configured to engage the neck of the medicament container when the delivery member shield is received in the receiving space, the grabber portion is configured to move from a first position in which the delivery member shield is attached to the neck to a second position in which the delivery member shield is detached from the neck. Also, in one embodiment, the needle shield remover and the delivery member shield are made of plastics, but are not limited thereto. The needle shield remover can be made of other suitable materials such as metal.

According to another aspect of the present disclosure, a medicament delivery device comprises a housing and a cap assembly configured to be mounted to the housing to cover a proximal opening of the housing comprising e.g. a needle. The cap assembly includes a cap and a needle shield remover configured to be assembled with the cap.

BRIEF DESCRIPTION OF DRAWINGS

In the following detailed description of the present disclosure, reference will be made to the accompanying drawings, of which

DETAILED DESCRIPTION

Figure 1:
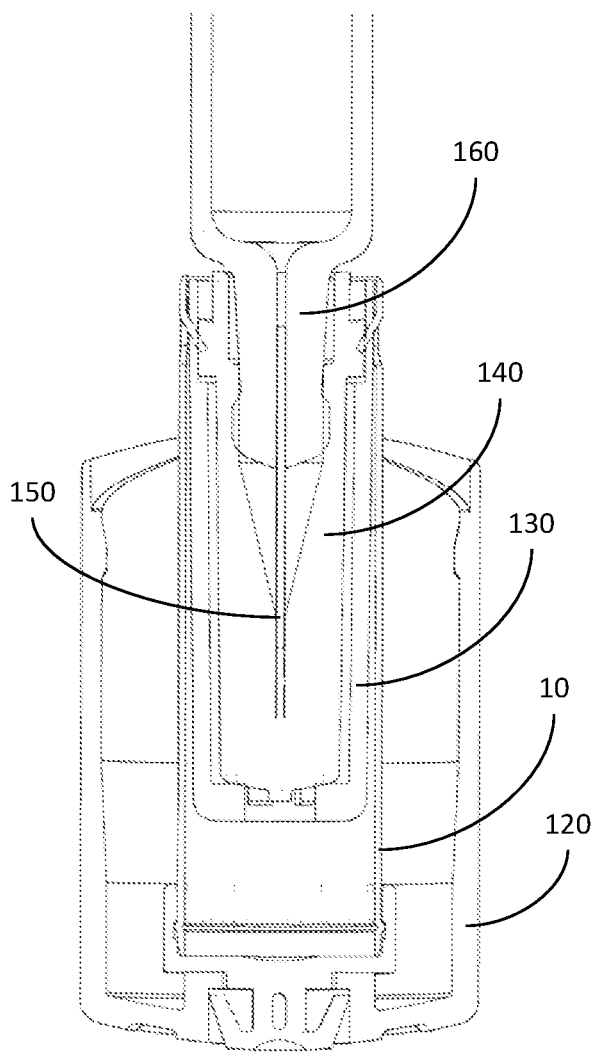
FIG. 1 shows a perspective view of a needle shield remover according to prior art.

FIG. 1 shows a needle shield remover 10 comprised in a cap 120. The cap 120 and the needle shield remover 10 are arranged on a rigid needle shield, or RNS 130, which covers a flexible needle shield, or FNS 140. A needle 150, of a syringe 160, is embedded in the FNS 140. The syringe 160 may be housed in a medicament delivery device (not shown), for instance an auto-injector. The needle shield remover 10 is attached to the cap 120 and comprises inwardly-projecting gripping members which engage the RNS 130, either by a distal end thereof or by engagement to a circumferential surface of the RNS 130, such that the movement of cap 120 away from the needle 150 results in pulling the RNS 130 and the FNS 140 away from the needle 150.

The present disclosure relates to a needle shield remover which is intended to be applied to known needle shields, for instance needle shields as shown in FIG. 1. The needle shield remover of the present disclosure is described in detail in conjunction with FIGS. 2-4.

Figure 2:
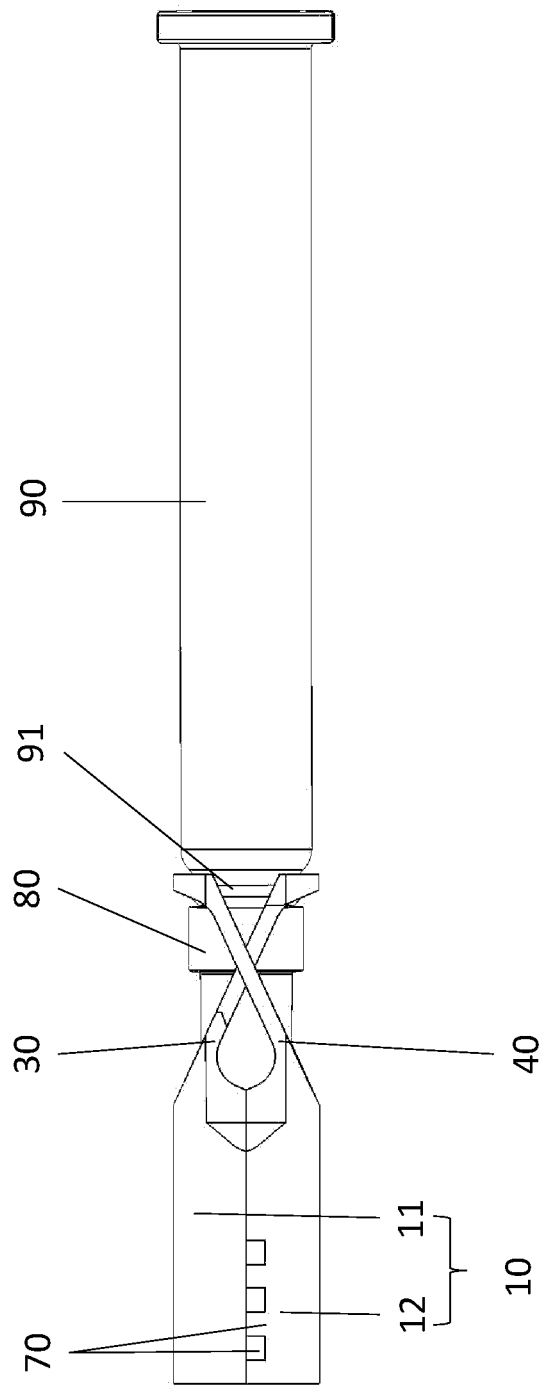
FIG. 2 shows a perspective view of a needle shield remover according to a first embodiment of the present disclosure.

Here please refer to FIG. 2 for the description on the interaction amongst the needle shield remover 10, needle shield 80, and medicament container 90. FIG. 2 shows a perspective view of a needle shield remover 10 according to a first embodiment of the present disclosure. The needle shield remover 10 includes a first portion 11 and a second portion 12 coupled together to form the needle shield remover 10. The first portion 11 and second portion 12 each includes a plurality of coupling members 70 configured to couple together so that the first portion 11 and second portion 12 together form the needle shield remover 10. The needle shield remover 10 includes a first grabber 30 extending from the first portion 11 and a second grabber 40 extending from the second portion 12.

As illustrated, the first grabber 30 and second grabber 40 extend obliquely and radially inward to cross each other and enclose at least a portion of the needle shield 80 placed on the syringe 90. The free ends of the first grabber 30 and second grabber 40 are configured to engage both the distal end of the needle shield 80 and the neck 91 of the syringe 90. In the present embodiment, the needle shield remover 10 is coupled with a cap (not illustrated) to be held and pulled by the user away from the syringe 90 in the proximal direction. Since the needle shield remover 10 and the cap are coupled, pulling the cap will also force the needle shield remove 10 to move in the proximal direction. This results in that the free ends of the grabbers 30, 40 are engaging the back end of the needle shield 80 and force the needle shield 80 to detach from the neck of the syringe 90. During the removal process, the needle shield 80 is always enclosed and trapped in the grabbers 30, 40.

Figure 3:
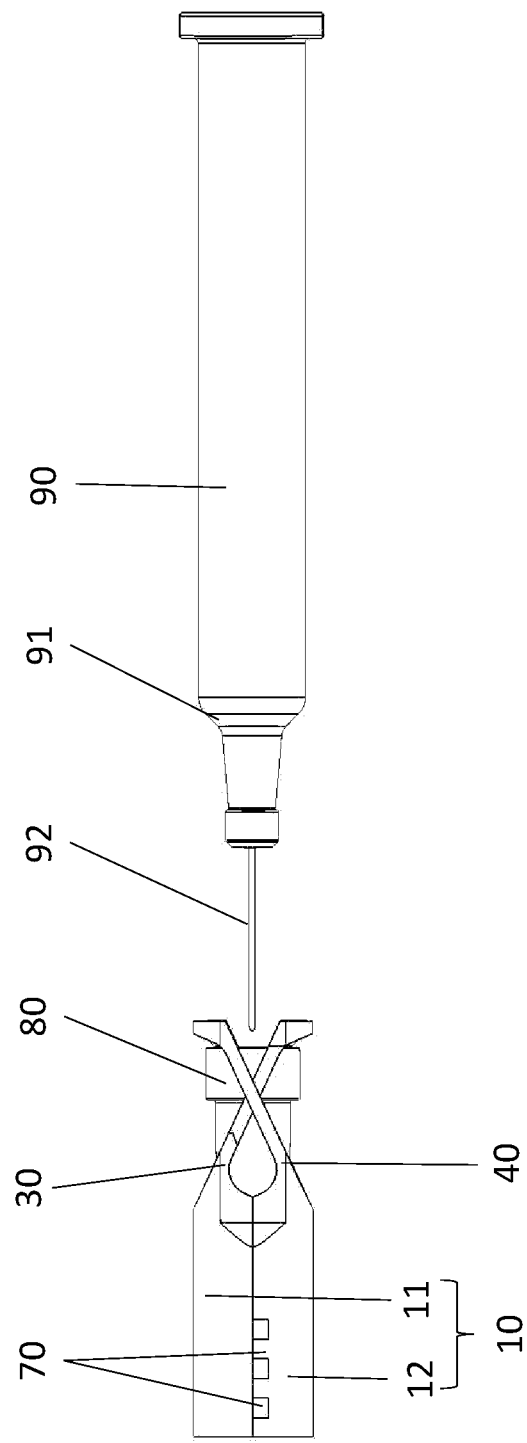
FIG. 3 shows a perspective view of a needle shield remover according to a first embodiment of the present disclosure.

FIG. 3 is another perspective view of a needle shield remover 10 according to a first embodiment of the present disclosure. As discussed above, the needle shield remover 10 is coupled with a cap (not illustrated) that can be pulled by a user in the proximal direction away from the syringe 90. The pull in the proximal direction not only moves the needle shield remover 10 away from the syringe 90, it also allows the end portions of the first grabber 30 and second grabber 40 to engage the distal end of needle shield 80. Said pulling and engagement force the needle shield 80 to detach from the neck 91 of the syringe 90 to subsequently reveal the needle 92 on the syringe 90.

Figure 4:
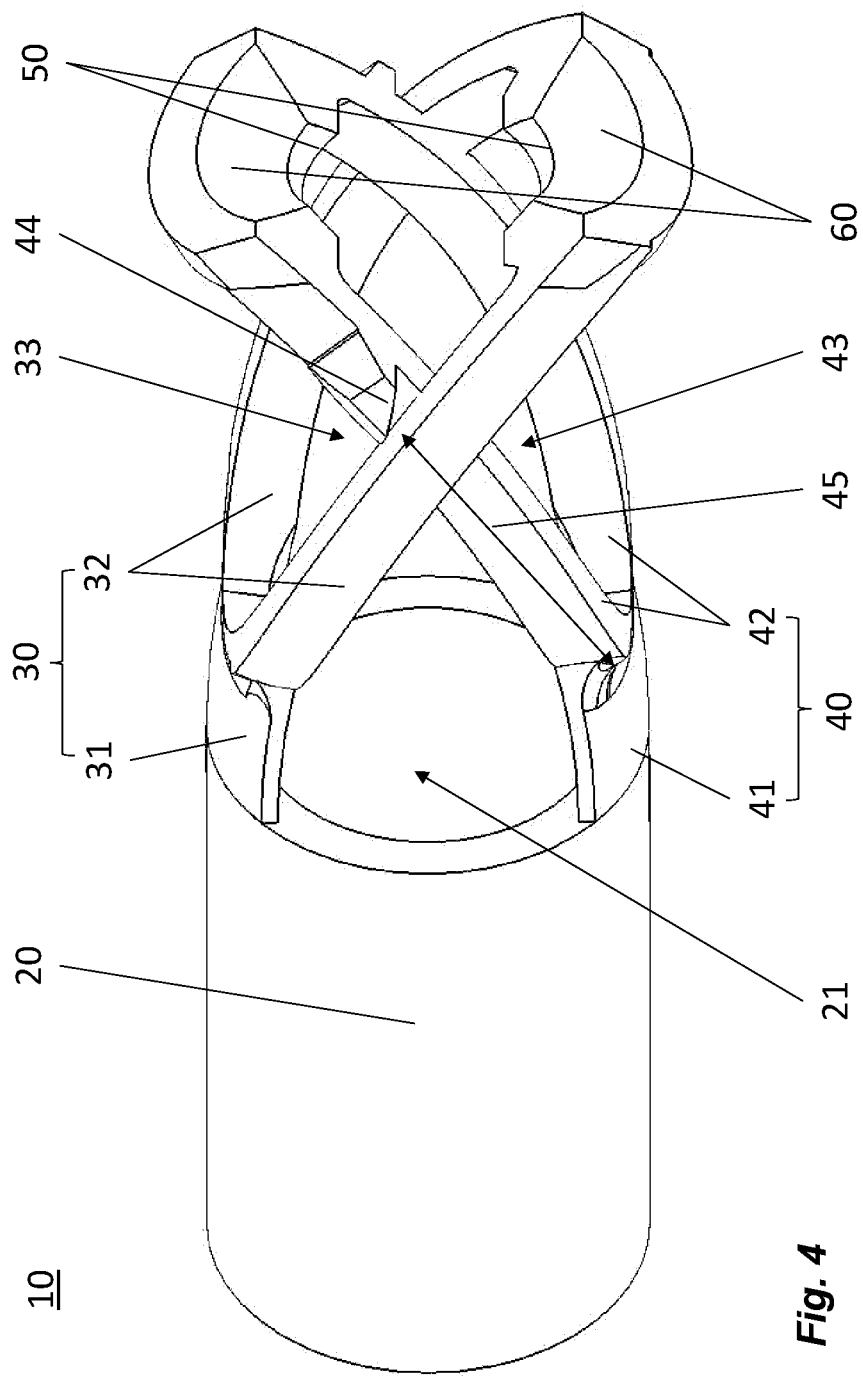
FIG. 4 shows a perspective view of a needle shield remover according to a second embodiment of the present disclosure.

FIG. 4 shows a needle shield remover 10 according to a second embodiment of the present disclosure. The needle shield remover 10 includes a main body 20 that has a tubular inner space 21 for accommodating at least a portion of the needle shield 80 in the main body 20 during assembly. In the present embodiment, the main body 20 is tubular in shape, but is not limited thereto. In other embodiments, the main body 20 can have other different shapes as long as its inner space is tubular to accommodate the needle shield 80. Also, the main body 20 in the present embodiment is made of plastics, but is not limited thereto. The main body 20 can also be made of other suitable materials such as metal.

On the other hand, the needle shield remover 10 further includes a first grabber 30 and second grabber 40 extending from the distal end of the main body 20. The first grabber 30 includes a first grabber connection 31 and a pair of first arms 32. The second grabber 40 also includes a second grabber connection 41 and a pair of second arms 42.

In this embodiment, the first grabber connection 31 and second grabber connection 41 connected to the main body 20 are layers of plastics extending from the main body 20 made of the same material. The layer-shaped connections 31, 41 allow the first grabber 30 and second grabber 40 to be radially flexible with respect to an axis passing through the centre of the main body 20. However, the first and second grabber connections 31, 41 extending from the main body 20 can be configured to have other flexible structures other than layer that also allows the grabbers 30, 40 to be radially flexible. Also, depending on the direction of force applied on the first grabber 30 and second grabber 40, the first and second grabbers 30, 40 can be made to flex radially inward and outward.

As illustrated in FIG. 4, the first grabber 30 includes a pair of first arms 32 extending from the first grabber connection 31 and meet together to form a first opening 33. On the other hand, the second grabber 40 includes a pair of second arms 42 extending from the second grabber connection 41, pass through the first opening 33, and then connect to form a second opening 43. The first grabber arms 32 and second grabber arms 42 cross each other to form a space configured to receive a needle shield 80. Both the first arms 32 and second arms 42 extend radially inward respectively from the first grabber connection 31 and second grabber connection 41 in order for the first grabber 30 and second grabber 40 to cross each other.

Also, to limit the degree that the first grabber 30 can be flex radially outward, the second grabber 40 includes a limiting member 44 on the side of both second arms 42 to create a limiting gap 45 that defines the degree that the first grabber 30 can be radially flexible. Thus, if a force moves the first arms 32 to flex radially outward eventually they will collide with the limiting members 44 and then cannot flex further radially outward. Also illustrated in FIG. 4, each of the first grabber 30 and second grabber 40 includes a grabber portion 50 configured to engage with the distal end of needle shield 80 after assembly and a neck portion 60 configured to engage the neck of a syringe 90.

When coupling a needle shield 80 on a syringe 90 (such as the one illustrated in FIG. 2) with the needle shield remover 10, the proximal end of needle shield 80 interacts with the free ends of the arms 32, 42 and pushes the arms 32, 42 to flex radially inward and increase the gap between the grabber portions 50 so that the needle shield 80 can pass through. The arms 32, 42 then flex further radially outward when the distal end of needle shield 80 passes the grabber portions 50. At that moment, the grabber portions 50 are in contact with the distal end of needle shield 80 and the neck portions 60 are in contact with the neck of syringe 90 similar to the configuration illustrated in FIG. 2. Thus, when user pulls the cap connected to the needle shield remover 10, the grabber portions 50 in direct contact with the distal end of needle shield 80 can bias the needle shield 80 to separate it from the syringe 90.

In the Figures, various engagement features for are shown for providing an engagement between one or more components of the drug delivery device for automatic and/or manual medicament delivery, e.g. at a self-administered injection. The engagement features may be any suitable connecting mechanism such as a snap lock, a snap fit, form fit, a bayonet, lure lock, threads or combination of these designs. Other designs are possible as well.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

The invention claimed is:

1. A needle shield remover comprising:
    a main body; and
    at least a flexible first grabber and at least a flexible second grabber extending from the main body, and being inclined in relation to a longitudinal axis such that they cross each other to define a grabber portion and form a receiving space configured to receive a delivery member shield,
    wherein the delivery member shield is attached to a neck of a medicament container and the grabber portion has a neck portion configured to engage the neck of the medicament container when the delivery member shield is received in the receiving space.

2. The needle shield remover of claim 1, wherein the main body includes:
    a first portion and the first grabber extending from the first portion; and
    a second portion and the second grabber extending from the second portion;
    wherein the first portion and the second portion are configured to couple together to form the main body.

3. The needle shield remover of claim 2, wherein the first portion includes at least one first coupling member and the second portion includes at least one second coupling member, the first and second coupling members are configured to engage each other to couple the first and second portions together to form the main body.

4. The needle shield remover of claim 1, wherein the first grabber includes a first opening configured to allow the second grabber to pass through and cross the first grabber.

5. The needle shield remover of claim 4, the second grabber including a second opening, wherein the first opening and the second opening are configured for the delivery member shield to pass through and at least partially enter the main body.

6. The needle shield remover of claim 4, wherein the second grabber includes a limiting member configured to engage the first grabber and limit a radial movement of the first grabber relative to the second grabber.

7. The needle shield remover of claim 1, wherein each of the first grabber and the second grabber includes a pair of arms extending from the main body and connects to form the grabber portion.

8. The needle shield remover of claim 1, wherein the grabber portion is configured to move from a first position in which the delivery member shield is attached to the neck to a second position in which the delivery member shield is detached from the neck.

9. The needle shield remover of claim 1, wherein the needle shield remover and the delivery member shield are made of plastics.

10. An assembly comprising:
    a syringe;
    a needle connected to a proximal end of the syringe;
    a needle shield covering the needle; and
    a needle shield remover according to claim 1 operatively engaged with the needle shield.

11. A needle shield remover comprising:
    a main body comprising a first portion and a second portion;
    a first flexible grabber extending in a distal direction from the first portion; and
    a second flexible grabber extending in a distal direction from the second portion, where the first and second flexible grabbers are inclined in relation to a longitudinal axis of the main body such that they cross each other to define a grabber portion and form a receiving space configured to receive a delivery member shield, and
    wherein the first and second portions are coupled together to form the main body, and
    wherein the delivery member shield is attached to a neck of a medicament container and the grabber portion has a neck portion configured to engage the neck of the medicament container when the delivery member shield is received in the receiving space.

12. The needle shield remover of claim 11, wherein the first flexible grabber includes a first opening, where the second flexible grabber extends through the opening to cross the first flexible grabber.

13. The needle shield remover of claim 11, wherein the second flexible grabber includes a limiting member that will engage the first flexible grabber to limit radial movement of the first flexible grabber relative to the second flexible grabber.

* * * * *